United States Patent [19]

Hüschelrath et al.

[11] Patent Number: 4,692,702

[45] Date of Patent: Sep. 8, 1987

[54] DEVICE WITH TWO GENERATORS FOR MEASURING THE GRADIENTS OF MAGNETIC FIELDS

[75] Inventors: Gerhard Hüschelrath, Laufach-Frohnhofen; Herbert Diehl, Erlensee, both of Fed. Rep. of Germany

[73] Assignee: Nukem GmbH, Hanau an Main, Fed. Rep. of Germany

[21] Appl. No.: 773,258

[22] Filed: Sep. 6, 1985

[30] Foreign Application Priority Data

Sep. 27, 1984 [DE] Fed. Rep. of Germany ....... 3435455

[51] Int. Cl.⁴ .................. G01R 33/06; G01R 33/022; G01N 27/87
[52] U.S. Cl. .................... 324/251; 307/309; 324/235; 338/32 H
[58] Field of Search ............... 324/207, 208, 235, 251, 324/117 H; 338/32 H; 307/309; 357/27; 360/112

[56] References Cited

U.S. PATENT DOCUMENTS

| 2,987,669 | 6/1961 | Kallmann | 324/251 |
| 2,988,650 | 6/1961 | Weiss | 324/251 X |
| 3,139,600 | 6/1964 | Rasmanis et al. | 338/32 H |
| 3,657,686 | 4/1972 | Masuda et al. | 324/251 X |
| 3,710,236 | 1/1973 | Halsey et al. | . |
| 4,349,814 | 9/1982 | Akehurst | 324/251 X |
| 4,395,677 | 7/1983 | Petersdorf | 324/117 H |
| 4,443,716 | 4/1984 | Avery | 324/117 H X |
| 4,518,918 | 5/1985 | Avery | 324/251 X |

FOREIGN PATENT DOCUMENTS

| 0125688 | 9/1980 | Japan | 338/32 H |
| 0007269 | 1/1984 | Japan | 324/251 |
| 0868765 | 5/1961 | United Kingdom | 324/251 |

Primary Examiner—Gerard R. Strecker
Attorney, Agent, or Firm—Cushman, Darby & Cushman

[57] ABSTRACT

The object of the invention is a device with two Hall generators (12, 14) for measuring the gradients of magnetic leakage fields in the non-destructive testing of materials. The two Hall generators (12, 14) are arranged at a distance from each other with their broad sides on a flat carrier substrate (18). They are positioned along a common line (36) with respect to which they each have the same alignment. Furthermore the two Hall generators are arranged close to the edges (40) of two opposite sides of the carrier substrate (18) that are free of connections.

5 Claims, 4 Drawing Figures

DEVICE WITH TWO GENERATORS FOR MEASURING THE GRADIENTS OF MAGNETIC FIELDS

FIELD OF THE INVENTION

The invention relates to a device with two Hall generators for measuring the gradients of magnetic fields.

BACKGROUND OF THE INVENTION

It is state of the art to use two Hall generators whose Hall voltages are subtracted from each other in order to measure the gradients of magnetic leakage fields in the non-destructive materials testing of materials by the leakage-flux method. The two Hall generators are arranged in parallel to each other in two different planes and overlap each other to some extent. The broad sides of the Hall generators are aligned at a small distance from the surface of the ferromagnetic body to be tested (U.S. Pat. No. 3,710,236). With this known arrangement, grain structure faults can be registered that are contained at least to some extent in one plane that passes vertically to the broad sides of the Hall generators and parallel to planes placed through the connecting points of the Hall electrodes.

SUMMARY OF THE INVENTION

The invention is based on the object of developing a device with two Hall generators for measuring the gradients of magnetic fields that allows as dense an arrangement as possible of several devices that are identical to each other with respect to the surface of the body to be tested at a small distance from its surface.

The object is solved in accordance with the present invention by the Hall generators being arranged with their broad sides on a flat carrier substrate at a distance from each other along a common line under equal alignment with respect to the line close to the edges of two opposite sides of the carrier substrate that are free of connections in each case. Since the Hall generators are no longer arranged with their broad sides one above the other but alongside each other, the thickness of the device is small. Consequently, considerably more devices can be arranged with their broad sides next to each other and along the surface of the body to be tested. The surface of the Hall generators arranged with their narrow sides arranged one above the other and projected onto the surface of the test body is less than is the case with two Hall generators arranged with their broad sides one above the other. This means that a finer allocation of the surface to the Hall generators is possible. It is therefore possible to localize defects more accurately. One of the two Hall generators can be arranged at a relatively slight distance from the surface of the body to be tested. The response sensitivity is thus increased. Relatively small defects in the test body can therefore still be detected.

In a preferred embodiment, the Hall generators are arranged in a housing with six connections of which two groups of three are arranged on narrow sides facing each other, two control electrodes of the Hall generators being joined together at one connection, while the two other control electrodes are joined to one connection each, and two Hall electrodes whose opposite polarities of the Hall voltages of the Hall generators are joined together and placed on a common connection accordingly, while the other Hall electrodes are each joined to one connection.

The Hall electrodes of the Hall generators are already joined together on the carrier substrate in a differential circuit. The nature of the link with the connections makes it possible to tap both the differences of the Hall voltages and also the individual Hall voltages at the connections. It is also possible to supply just a control current to the control electrodes through the connections.

In this case the connections that are each joined with a control electrode must be connected in parallel. On the other hand, it is also possible to feed in two separate control currents that must then be referred to a common potential at the control electrodes that are joined together. In the latter case, the control electrodes joined together in the housing should preferably be connected to ground potential. With a minimum of connections in the housing, the Hall generators can thus be incorporated in various types of circuit.

The Hall generators are advantageously made from gallium arsenide. Such Hall generators produce high Hall voltages within relatively small dimensions. The housing is made preferably of plastic material. The device can be made as low cost with a plastic housing.

It is advantageous to arrange the center lines of the rectangular Hall generators at a distance of about 0.55 mm respectively from the nearest edge of the housing having no connections. It has been found that this spacing can be achieved taking into consideration the circumstances of the carrier substrate, the electrodes of the Hall generator, the connecting leads to the electrodes and the fastening between carrier substrate and plastic housing. On account of this small spacing, the respective Hall generator can be mounted with its narrow side very close to the surface of the body to be tested, and this results in improved measuring sensitivity.

The housing preferably has a thickness of about 0.8 mm. Numerous housings can therefore be put together into groups with their broad sides next to each other, where each individual housing takes up only a small area on the surface of the body to be tested. Grain structure faults established by a test probe consisting of the two Hall generators contained in a housing can therefore be localized exactly on the surface.

In another preferred embodiment the spacing between the centers of the two Hall generators is about 2.5 mm. Considering the connections arranged in a row in groups of three in the housing, this spacing is sufficient to allow the probe to be installed in a small space.

BRIEF DESCRIPTION OF THE DRAWING

Further details, features and advantages of the invention are given in the following description of a typical embodiment illustrated by a drawing.

The figures show.

DETAILED DESCRIPTION OF THE INVENTION

Figure 1:
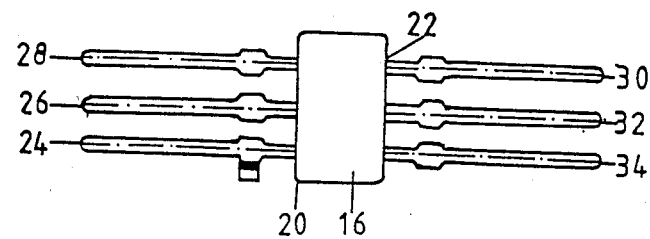
FIG. 1 a test probe with two Hall generators viewed from above.
Figure 2:
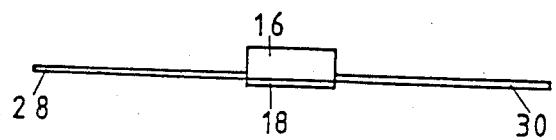
FIG. 2 the test probe in accordance with FIG. 1 shown as a side view.
Figure 3:
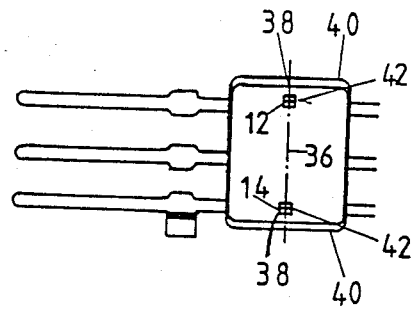
FIG. 3 a test probe viewed from above and showing the positions of the Hall generators, and FIG. 4 a circuit diagram of the arrangement consisting of the Hall generators, the connections of a housing and connecting leads.

Shown in FIGS. 1-3 are two Hall generators 12, 14 made of gallium arsenide. They are arranged within the housing 16 shown in FIG. 1 on a carrier substrate 18. The housing 16 is made of plastic material and has a flat rectangular shape. On two opposite facing narrow sides 20, 22 of the housing 16 connections 24, 26, 28, 30, 32 and 34 are arranged in groups of three in a row next to each other respectively. The connections 24 to 34 may be made of straight metal pins with rectangular cross-section. The width of the metal pins 24 to 34 is 0.6 mm in each case and the thickness is between 0.15 and 0.2 mm. The length and width of the housing 16 are approx. 3×4 mm.

The carrier substraight 18 is a flat wafer. In one plane on the surface of the wafer the Hall generators 12, 14 are arranged at a distance from each other longitudinally along a common line 36 which is represented by a dash-dotted line in FIG. 3. The Hall generators 12, 14 are made up of rectangular gallium arsenide wafers that are located at the same angle with respect to line 36. The gallium arsenide wafers are arranged each with one edge 38 close to the edge 40 of two narrow sides of the housing 16 that are not provided with connections 24 to 34. The spacing between the edges 40 and the center lines 42 each of which pass through the center of the gallium arsenide wafers parallel to the edges 40 is about 0.55 mm. Between the two center lines 42 there is a distance of about 2.55 mm. The height of the arrangement consisting of the carrier substrate 18 and the plastic housing is about 0.8 mm.

Figure 4:
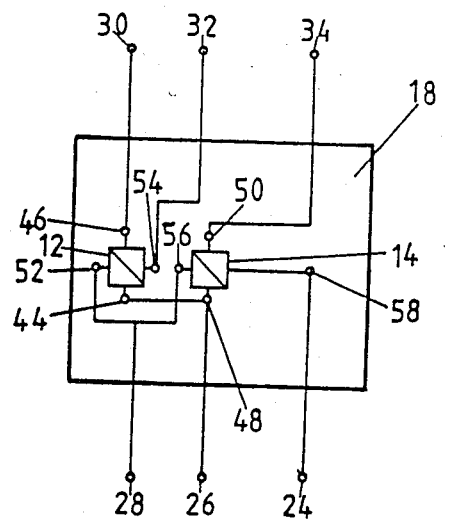

As shown in FIG. 4, the Hall generators 12, 14 contain control electrodes 44, 46 and 48, 50 respectively. The control electrodes 44, 48 are joined together and placed jointly to connection 26. The control electrodes 46, 50 are joined with connections 30 and 34 respectively. Furthermore the Hall generators 12, 14 contain Hall electrodes 52, 54, 56, 58 respectively. The two Hall electrodes 52, 56 are joined together and placed on connection 28. The Hall electrodes 54, 58 are joined with connection 32 and 34 respectively. The connection between the Hall electrodes of Hall generators 12, 14 is selected so that the Hall voltages have opposite polarities.

The difference between the Hall voltages is therefore already available at connections 24 and 32. Each individual Hall voltage can however also be tapped on its own at the connections 28 and 32 or 28 and 24.

It is possible to supply the two Hall generators 12, 14 through connection 26 and the connection 30, 34 that must be joined together with a control current that splits up over the two Hall generators. A separate control current can however also be supplied to the Hall generator 12 and 14 through the connections 30, 34. The control currents then merge and flow together to connection 26 at which the two control current generators must be connected with one pole each. It is advisable to apply ground potential to connection 26.

With the device shown in FIGS. 1 to 4, that is suitable as a test probe in particular for leakage-flux measurements when testing ferromagnetic bodies with magnetic fields, the Hall generators 12, 14 can be fitted with their broad sides vertical to the surface element to be tested. In addition one of the Hall generators 12 or 14 can be arranged at a small distance from the surface of the test place. This also allows relatively small stray fluxes and thus small faults in the grain structure of the test body to be recognized. Owing to the small spatial expansion of the narrow side of the respective Hall generator 12, 14 projected onto the surface of the test piece, it is possible to accurately allocate faults to the various sections of the test piece.

Numerous housings 14 can be arranged with their broad sides next to each other along a strip of the surface on the body to be tested. The body to be tested is then moved transversely across the row of test probes. A movement along the row is not necessary in order to be able to establish faults.

The allocation of faults to the respective locations results from the geometrical position of the Hall probe establishing the fault in relation to the body.

We claim:

1. A device with two multiple electrode Hall generators for measuring the gradients of magnetic leakage fields in the non-destructive testing of materials, characterized in that the Hall generators comprise thin rectangular wafers each arranged with a broad surface thereof lying on a flat rectangular shaped, four sided substrate, said Hall generators being spaced apart longitudinally along a common line with the same alignment to the line respectively and close to the periphery of two opposite sides of the substrate respectively, the two sides being free of connections, a rectangular-shaped, four sided housing having six external connections, three of which are arranged on one side of the rectangular-shaped housing and three of which are arranged on the opposite side, the other two opposite sides of said housing being free of external connections, said housing overlying the substrate, with the two opposite sides of said substrate which are free of connections being adjacent the opposite sides of said housing which are free of external connections, respectively, with one control electrode of each Hall generator being together joined to a first external connection, with one other control electrode of each Hall generator being joined, respectively, to second and third external connections, with two Hall electrodes, one from each Hall generator, whose opposite polarities correspond respectively to the Hall voltages of said two Hall generators, being joined together to a fourth external connection, and with the other Hall electrode of each Hall generator being, respectively, joined to fifth and sixth external connections.

2. Device in accordance with claim 1, characterized in that the Hall generators are made of gallium arsenide.

3. Device in accordance with claim 1, characterized in that the center lines of the rectangular wafers of the Hall generators are arranged at a distance of about 0.55 mm from the respectively nearest side of the housing that is free of connections.

4. Device in accordance with claim 1, characterized in that the housing including the carrier substrate has a thickness of about 0.8 mm.

5. Device in accordance with claim 1, characterized in that the distance between the centres of the two Hall generators is about 2.55 mm.

* * * * *